(12) United States Patent
Krieger et al.

(10) Patent No.: US 12,245,831 B2
(45) Date of Patent: Mar. 11, 2025

(54) APPARATUS AND METHOD FOR ROBOTIC PROCEDURES WITH MAGNETIZABLE TOOLS

(71) Applicants: THE JOHNS HOPKINS UNIVERSITY, Baltimore, MD (US); University of Maryland, College Park, MD (US); Weinberg Medical Physics, Inc, North Bethesda, MD (US)

(72) Inventors: Axel Krieger, Fulton, MD (US); Yancy Diaz-Mercado, College Park, MD (US); Xiaolong Liu, Baltimore, MD (US); Matthew Fan, College Park, MD (US); Lamar Mair, Baltimore, MD (US); Irving Weinberg, Chevy Chase, MD (US); Sagar Chowdhury, Peoria, IL (US); Will Pryor, Baltimore, MD (US); Yotam Barnoy, Baltimore, MD (US); Suraj Raval, College Park, MD (US); Önder Erin, Baltimore, MD (US)

(73) Assignees: THE JOHNS HOPKINS UNIVERSITY, Baltimore, MD (US); UNIVERSITY OF MARYLAND, College Park, MD (US); WEINBERG MEDICAL PHYSICS, INC, North Bethesda, MD (US)

( * ) Notice: Subject to any disclaimer, the term of this patent is extended or adjusted under 35 U.S.C. 154(b) by 271 days.

(21) Appl. No.: 17/721,575

(22) Filed: Apr. 15, 2022

(65) Prior Publication Data
US 2022/0338944 A1  Oct. 27, 2022

Related U.S. Application Data

(60) Provisional application No. 63/175,657, filed on Apr. 16, 2021.

(51) Int. Cl.
*A61B 34/32* (2016.01)
*A61B 5/055* (2006.01)
(Continued)

(52) U.S. Cl.
CPC .............. *A61B 34/32* (2016.02); *A61B 5/055* (2013.01); *A61B 34/73* (2016.02);
(Continued)

(58) Field of Classification Search
CPC .......... A61B 34/73; A61B 2017/00398; A61B 34/32; A61B 2034/2055; A61B 5/055; A61B 90/361; A61B 2090/378
See application file for complete search history.

(56) References Cited

U.S. PATENT DOCUMENTS 9,694,196 B2  7/2017  Weinberg et al.
10,290,404 B2  5/2019  Mair et al.
(Continued)

OTHER PUBLICATIONS

Baharlou, S. (Authorized officer), International Preliminary Report on Patentability in corresponding International Application No. PCT/US2022/024965 mailed on Oct. 26, 2023, 8 pages.
(Continued)

*Primary Examiner* — Chao Sheng
(74) *Attorney, Agent, or Firm* — MH2 Technology Law Group LLP (57) ABSTRACT

Methods and apparatuses are provided for performing surgery and other interventional procedures on human and non-human animals with a semi-autonomous and/or fully autonomous robotic system. The methods and apparatuses include a system for controlling magnetic fields to dynamically detect the location of magnetizable tools and to manipulate said tools in order to obtain a favorable therapeutic or diagnostic outcome.

18 Claims, 4 Drawing Sheets

(51) Int. Cl.
  *A61B 34/00*   (2016.01)
  *A61B 34/20*   (2016.01)
  *A61B 17/00*   (2006.01)
  *A61B 90/00*   (2016.01)

(52) U.S. Cl.
  CPC .............. *A61B 2017/00398* (2013.01); *A61B 2034/2055* (2016.02); *A61B 90/361* (2016.02); *A61B 2090/378* (2016.02)

(56) References Cited

U.S. PATENT DOCUMENTS

| | | | |
|---|---|---|---|
| 10,908,240 | B2 | 2/2021 | Weinberg |
| 2002/0032451 | A1 | 3/2002 | Tierney et al. |
| 2004/0167548 | A1* | 8/2004 | Bonutti .............. A61B 17/0401 606/144 |
| 2008/0161677 | A1 | 7/2008 | Sutherland et al. |
| 2009/0149867 | A1 | 6/2009 | Glozman et al. |
| 2014/0058406 | A1 | 2/2014 | Tsekos |
| 2017/0227617 | A1* | 8/2017 | Weinberg .............. G01R 33/381 |
| 2019/0038370 | A1* | 2/2019 | Weinberg .............. A61B 10/04 |
| 2020/0289217 | A1 | 9/2020 | Denlinger et al. |
| 2022/0338944 | A1 | 10/2022 | Krieger et al. |

OTHER PUBLICATIONS

Romano, Alper (Authorized officer), International Search Report and Written Opinion issued in International Patent Application No. PCT/US2022/024965 mailed Jun. 30, 2022, 9 pages.

Ester, Martin et al. "A density-based algorithm for discovering clusters in large spatial databases with noise." kdd. Vol. 96. No. 34. 1996.

Fan, Matthew et al. "Towards autonomous control of magnetic suture needles." 2020 IEEE/RSJ International Conference on Intelligent Robots and Systems (IROS). IEEE, 2020.

Fischler, Martin A. et al. "Random sample consensus: a paradigm for model fitting with applications to image analysis and automated cartography." Communications of the ACM 24.6 (1981): 381-395.

Mair, Lamar O. et al. "Magnetosuture: Tetherless manipulation of suture needles." IEEE transactions on medical robotics and bionics 2.2 (2020): 206-215.

Paszke, Adam et al. "Pytorch: An imperative style, high-performance deep learning library." Advances in neural information processing systems 32 (2019).

Pryor, Will et al. "Localization and control of magnetic suture needles in cluttered surgical site with blood and tissue." 2021 IEEE/RSJ International Conference on Intelligent Robots and Systems (IROS). IEEE, 2021.

Sandler, Mark et al. "Mobilenetv2: Inverted residuals and linear bottlenecks." Proceedings of the IEEE conference on computer vision and pattern recognition. 2018.

* cited by examiner

APPARATUS AND METHOD FOR ROBOTIC PROCEDURES WITH MAGNETIZABLE TOOLS

CROSS REFERENCE AND PRIORITY CLAIM

This application claims priority to U.S. Provisional Patent Application Ser. No. 63/175,657, entitled "APPARATUS AND METHOD FOR ROBOTIC PROCEDURES WITH MAGNETIZABLE TOOLS" filed 16 Apr. 2021, the entirety of which is incorporated by reference.

FIELD

Disclosed examples may be used to obtain a favorable therapeutic or diagnostic outcome in procedures performed on human and non-human animals.

BACKGROUND

Manipulation of surgical or other minimally invasive instruments typically requires the application of force on tissues for controlling the position or action of the instrument(s). In the case of suturing for closing a wound or incision, force is applied to the surgical instrument, such as a suture needle and suture thread, for the purposes of moving the suture needle towards the indicated wound or incision and, in the case of a suture, inserting the needle through the tissue, often repeatedly, for the purposes of passing the thread through the tissue and applying force to close the wound or incision. During each pass through the tissue, force is applied for the tightening of the suture closure. Similarly, for other surgical procedures involving a needle and suture thread, such as ligation, force is applied to move the needle to the desired site of action and then, as in the course of ligation, to repeatedly encircle a tissue or tissue section, applying force during each encircling passage.

In the field of surgical robotics, force can be transferred from the hands of a human surgeon into the robotic arms and end effectors of a surgical robotic apparatus. In such settings, joints and end effectors receive input guidance from surgeons. In some cases, the surgical robotic apparatus may perform a procedure partially or fully autonomously based on imaging information. Force is applied via mechanical contact between the end effector of the surgical robot and the surgical instrument. For procedures taking place inside the body cavity, maintaining a mechanical linkage with the surgical tool may require numerous ports of entry for surgical instrument manipulation.

In some procedures, minimizing the number and size of inserted surgical manipulators is advantageous for decreasing tissue damage, simplifying a procedure, or increasing access to a specific tissue or organ inside the body. Additionally, for surgical procedures in pediatric or neonatal settings in which there may be insufficient tissue to use physical manipulators, wireless manipulation of surgical instruments may prove beneficial. In such procedures, an untethered or wireless method of applying force to a surgical tool, such as a suture needle, may provide benefits for the patient and the surgical team.

SUMMARY

Disclosed examples provide methods and apparatuses for performing surgery and other interventional procedures on human and non-human animals with a semi-autonomous and/or fully autonomous robotic system. The method and apparatus include a system for controlling magnetic fields to dynamically detect the location of magnetizable tools and to manipulate said tools in order to obtain a favorable therapeutic or diagnostic outcome.

In accordance with at least some examples, an apparatus comprises a controller, camera, and magnetic actuators. One or more magnetizable tools are manipulated by the magnetic actuators robotically using information about the state of the magnetizable tool collected by the camera.

In accordance with at least some examples, a method of guiding therapeutic or diagnostic procedures in a human or non-human animal comprises manipulating a magnetizable tool by one or more magnetic actuators under closed-loop control. The closed-loop control uses images that provide information about the state of the magnetizable tool.

BRIEF DESCRIPTION OF FIGURES

Aspects and features of the invention are described in connection with various figures, in which.

DETAILED DESCRIPTION

The present invention will now be described in connection with one or more examples. It is intended for the examples to be representative of the invention and not limiting of the scope of the invention. The invention is intended to encompass equivalents and variations, as should be appreciated by those skilled in the art.

Reference is made to the following publications, incorporated herein by reference: ("MagnetoSuture: Tetherless Manipulation of Suture Needles", by L. O. Mair et al, in the IEEE Transactions on Medical Robotics Bionics, Vol. 2, No. 2, May 2020, pages 206-215, and referred to as IEEE 2019), ("Towards Autonomous Control of Magnetic Suture Needles", by M. Fan et al, presented at the 2020 IEEE/RSJ International Conference on Intelligent Robots and Systems, held virtually in October 25-29, and referred to as IROS 2020), and ("Localization and Control of Magnetic Suture Needles in Cluttered Surgical Site with Blood and Tissue", by W. Pryor et al, in IEEE/RSJ International Conference on Intelligent Robots and Systems (IROS), held Sep. 27-Oct. 1, 2021, DOI 10.1109/IROS51168.2021.9636441, and referred to as IROS 2021) in the disclosure.

Figure 1:
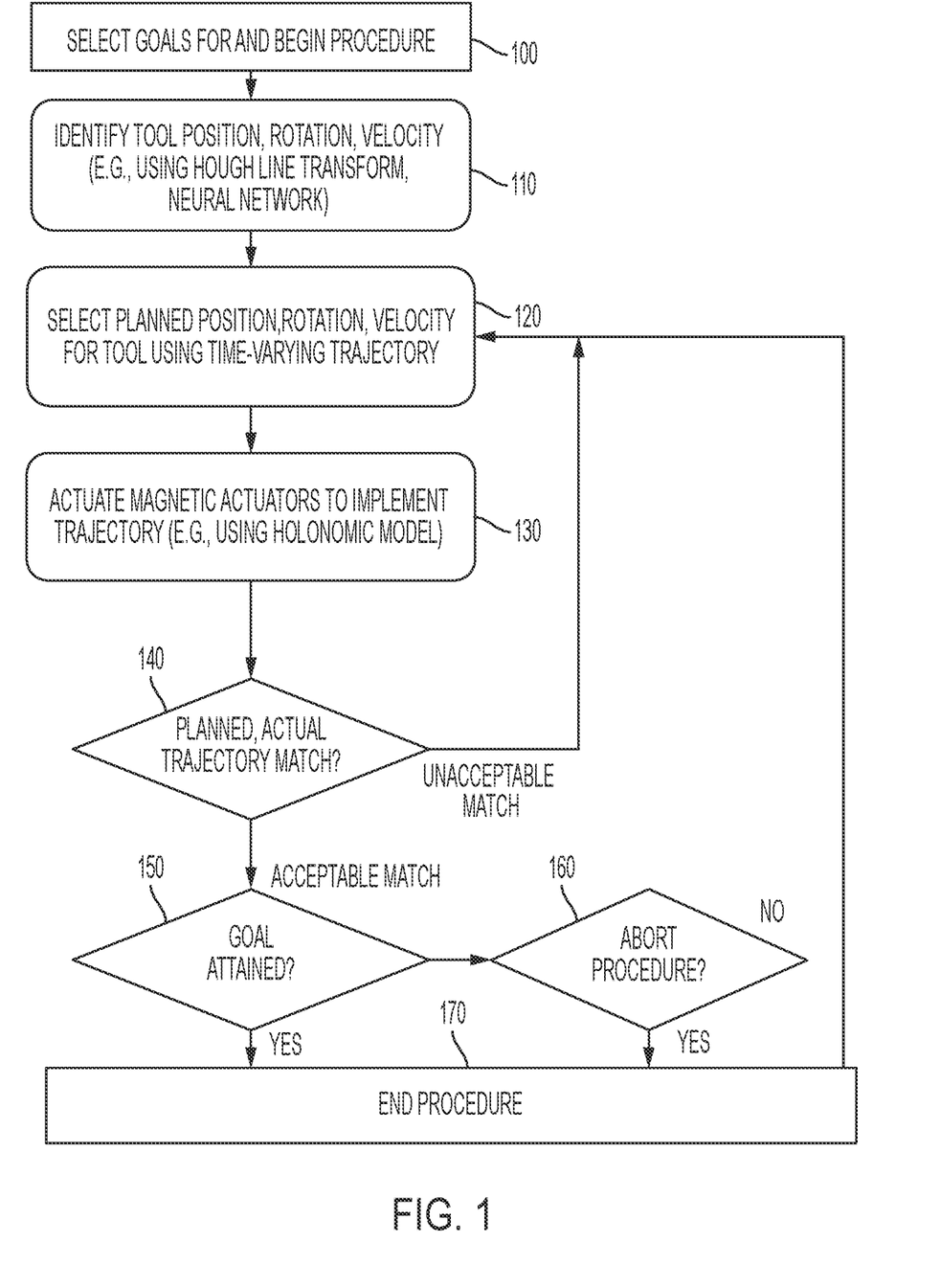
FIG. 1 illustrates an example of a method of guiding therapeutic or diagnostic procedures in accordance with disclosed examples.

FIG. 1 illustrates method operations of guiding therapeutic or diagnostic procedures in accordance with disclosed examples. As shown in FIG. 1, a user (for example, a surgeon) selects goals for a robotic procedure and initiates the procedure at operation 100. Control then proceeds to 110, at which a computer, optionally, under control of a user or operating in an automated or semi-automated manner, identifies the position, rotation, and velocity of one or more tools in a region-of-interest ("ROI").

An ROI is defined as a region of a body in which a procedure is to be performed, or in which access may be required in order to perform a procedure in another location.

A computer, optionally, under control of a user or operating in an automated or semi-automated manner, selects the planned position, rotation, and velocity of the tool(s), optionally using a time-varying trajectory at 120. Magnetic actuators (for example, electromagnets, or electropermanent magnets, or coils) are then used to create magnetic fields in the ROI to implement the trajectory at 130 that was planned at 120. The planned and actual trajectories (optionally including position, rotation, velocity) are compared at 140, and if acceptable match, then proceed to determining of the goal(s) are attained at 150. Otherwise, the method then returns to operation 110. If the user and/or computer decides that the goal(s) have been attained at 150, the robotic procedure ends at 170. If the user and/or computer decides that goal(s) have not been attained at 150 and the user and/or computer decides that robotic procedure should be aborted at 160, and the robotic procedure ends at 170, If the user and/or computer decides that goal(s) should not be aborted the method operations return to operation 110.

For example, consider the scenario when a user (for example, a surgeon) selects goals for a robotic procedure and initiates the procedure at 100. A computer, optionally, under control of a user or operating in an automated or semi-automated manner, identifies the position, rotation, and/or velocity of one or more magnetizable tools in a spatial region-of-interest ("ROI") in the body of a human or non-human animal at 110. The ROI may be selected by the user.

Figure 2:
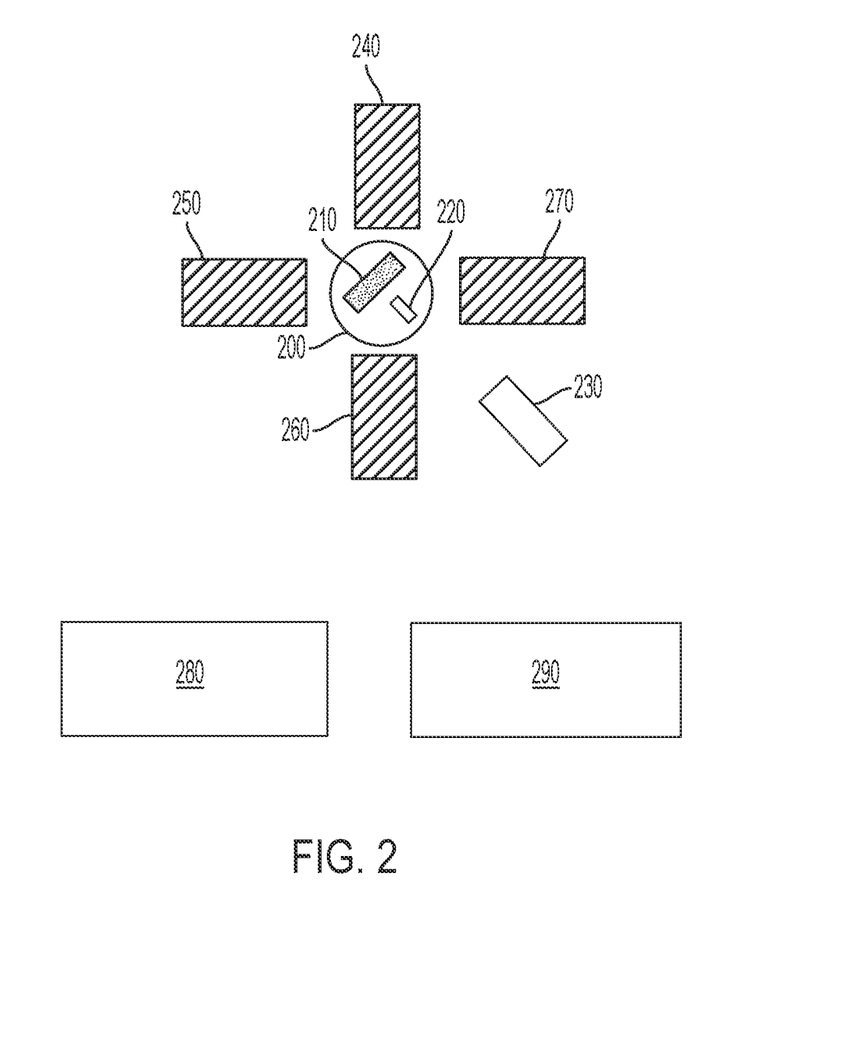
FIG. 2 illustrates an apparatus according to the disclosed examples.

In accordance with at least one example, the position, rotation, and/or velocity of one or more magnetizable tools may be selected with the aid of a computer using an imaging device such as a camera or an MRI or another imaging device described with reference to FIG. 2. FIG. 2 provides an illustration of an example of an apparatus, including a ROI 200, a tissue 210, a magnetizable tool 220, a camera 230 for describing the location and condition of the tool and/or tissue, an array of magnetic actuators 240, 250, 260, 270, a computer 280 and a controller 290 of the array of magnetic actuators. The controller 290 may include one or more power supplies and computers.

It should be understood that machine learning and classical and modern control techniques may be applied to both the localization/state estimation and/or control of the tool. Examples of applicable machine learning techniques for localization include artificial neural nets (ANN) and deep learning approaches, their combination with classical computer vision approaches, or other localization methods. Examples of applicable machine learning techniques for control include continuous-domain reinforcement learning approaches such as soft actor-critic (SAC) and proximal policy optimization (PPO), or other machine learning techniques. Examples of applicable classical control techniques include proportional-derivative (PD) control, proportional-integral-derivative (PID) control, proportional (P) control, integral (I) control, derivative (D) control, proportional-integral (PI) control, or other control methods. Examples of applicable modern control techniques include robust adaptive control, Lyapunov approaches, linear quadratic (LQ) control, control barrier function (CBF) control, linear matrix inequality (LMI) methods, or other control methods. Examples of applicable state estimation techniques include Luenberger observers, Kalman filters, or other estimator methods.

With reference to FIG. 2, it should be understood that wires, cables, or wireless connections may connect some or all of components 240-290. Although FIG. 2 only shows four actuators, the array of magnetic actuators may include more than four actuators with different placements. The imaging function of a camera 230 may be via optical, ultrasound, or magnetic resonance imaging (MRI) equipment, or by a combination thereof. It should be understood that the term "optical" includes ultraviolet, infrared or other portions of the electromagnetic spectrum, and that fluorescent markers may have a visible signal with the camera.

MRI equipment may be implemented in the camera by actuating the array 240-270 in conjunction with radiofrequency antennas (not shown). It is understood that the MRI and tool manipulation functions may be interleaved, as has been described using electropermanent magnets, as in U.S. Pat. No. 10,908,240, "METHOD FOR ACQUIRING AN IMAGE AND MANIPULATING OBJECTS WITH MAGNETIC GRADIENTS PRODUCED BY ONE OR MORE ELECTROPERMANENT MAGNET ARRAYS" incorporated herein by reference. It should also be understood that the MRI may provide information concerning the state of the tool with respect to position, rotation, velocity, and magnetization.

In accordance with at least some examples, the controller 290 may combine multiple streams of data for more accurate control and manipulation of the needle. One important stream of data is information extracted from images of the needle's surroundings that provides the controller 290 with a density map of the surrounding tissues. Such a density map informs the controller 290 of the expected force requirements for moving within a specific region of the sample space or surgical space. Another stream of information may be real time information regarding the force-translation or force-rotation relationships occurring, in real time, when the system applies forces and torques to the needle. Data on the motion response may be used to update machine learning algorithms utilized by the controller 290 about the forces required to perform a given motion.

It should be understood that the controller 290 may be of the closed loop type that uses images and pre-defined needle path information for guiding a needle. The controller operations may include establishing a coordinate system and modeling magnetic fields generated by arrays of electromagnets. Such models may include any of the various techniques used in modeling fields from windings of current carrying elements. In some examples, the controller 290 may include feedback linearizing controller components, which map linear and rotational velocities based on images.

In at least some examples, needle pose may be estimated by Hough Line Transform. Pre-processing and post-processing of images collected by the system may be scaled, filtered, thresholded, averaged, or otherwise modified so as to be useful or efficient for the controller software to perform its function of accurately manipulating the pose and velocity of the needle. Hough Line Transform approaches may be used alone or may be used in conjunction with other approaches. Additionally, other feature extraction techniques (e.g., partial least squares, principal component analysis, independent component analysis, or other techniques) may be used alone, or in combination with each other, for determining the location of the needle. Likewise, individual or combinations of feature extraction techniques may be used for determining the location of the suture thread in the sample area.

Turning to the specifics of operations performed in accordance with various disclosed examples, the ROI, position, rotation, and/or velocity of one or more magnetizable tools may be described mathematically as the domain of operation, wherein the interior of the dish or work space, denoted by $D \subset \mathbb{R}^2$, is a circular area of radius $r_{dom}$ centered at the origin. Consider the general setting of m electromagnets (EM) whose centers are located at $r_k \in \mathbb{R}^d$, $k \in \{1, \ldots, m\}$, without loss of generality assume that they are uniformly spaced a distance $r_{em} = \|r_k\|$ from the origin. As stated above, disclosed example operations assume these electromagnets are aligned such that their axes of symmetry intersect at the origin, i.e., that their axes of symmetry are $\hat{r}_k = r_k / r_{em}$.

In accordance with at least one example, the tool is a needle with its state described by centroid of a needle $r \in D$ and its heading (in the north pole direction) given by $\theta$ by manipulating external magnetic fields acting on the needle through the controlled currents of the m electromagnets. For convenience, the state of the needle may be denoted as $x = [r^T, \theta]^T$.

In implementation, identification of the state of the tool may not be simple due to nearby materials in the ROI. Thus, in accordance with at least one example, identification may be implemented though segmentation, as in an example using a neural network process involving encoder blocks, for example, as described in the publication submitted to the 2021 IEEE/RSJ International Conference on Intelligent Robots and Systems (IROS 2021, submission #830) (incorporated by reference).

More specifically, the network may include five MobileNetV2 encoder blocks, as described in M. Sandler, A. Howard, M. Zhu, A. Zhmoginov, and L. Chen, *Mobilenetv2: Inverted residuals and linear bottlenecks,* 2018, in IEEE/CVF Conference on Computer Vision and Pattern Recognition, pages 4510-4520 (incorporated by reference), wherein each encoder block halves the width and height of an image, and increases the number of features to levels prescribed by the MobileNetV2 architecture. Following these encoder blocks may be an equal number of decoder blocks, which double the width and height of the image while decreasing the number of features. In implementation, each decoder block may include two repetitions of {convolution, batch normalization, rectified linear unit (ReLU)}. A skip connection may connect each encoder block to its corresponding decoder block, thereby enabling the decoder to process information from multiple resolution levels. A final layer may add a convolution to reduce the number of features to one. Thereafter, application of a sigmoid function, may yield a segmentation mask for either 'needle' or 'background'. See an example of one particular implementation for construction a final set of needle points, as described in ("Localization and Control of Magnetic Suture Needles in Cluttered Surgical Site with Blood and Tissue", by W. Pryor et al, in IEEE/RSJ International Conference on Intelligent Robots and Systems (IROS), held Sep. 27-Oct. 1, 2021, DOI 10.1109/IROS51168.2021.9636441, and referred to as IROS 2021).

Algorithm 1 Construction of Final Set of Needle Points

1. Sort clusters in decreasing order by number of points
2. Needle_points:=largest_cluster
3. for cluster sets do
4. if cluster≠largest_cluster then
5. D:=max ($\|x_e - x_n\|$), $\forall x_e \in$ cluster, $\forall x_n \in$ needle_points
6. If d<1.1×needle_length then
7. Append cluster to needle_points
8. return needle_points The use of these values is described in See. III-D. We train the segmentation head of the network using dice loss [25], which emphasizes small classes (such as our needle) relative to the whole image, and binary cross-entropy loss for classification head. The two are combined with equal weights into one loss. We used a learning rate of 0.0001 and a Root Mean Square Propagation (RMSProp) optimizer running for 20 epochs.

In some examples, the segmentation problem may be simplified by pre-processing the images, as described in the paper submitted to 2021 IEEE/RSJ International Conference on Intelligent Robots and Systems (IROS 2021, submission #830). For example, during pre-processing, images may be collected at a frame rate from 0.01 frames per second to 100,000 frames per second. For each sampled frame, the image may be cropped to 1024×1024 pixels, which is the approximate size of a petri dish or a sample ROI in a sample dataset. The image may then be masked by a circle with an actual radius of such a petri dish.

Both the imaging cropping and masking may be centered at the dish center, which may be manually calibrated together with the radius. Images may then be downsampled to 512×512 pixels, and normalized per channel of RGB to a mean of (0.485, 0.456, 0.406) with a standard deviation of (0.229, 0.224, 0.225), for compatibility with pretrained weights distributed by PyTorch, as described in A. Paszke, S. Gross, F. Massa, et al., *Pytorch: An imperative style, high-performance deep learning library,* in Advances in Neural Information Processing Systems, 2019, pages 8024-8035 (incorporated by reference). Such weights may be the result of training a MobileNetV2 network on the ImageNet database.

In some examples, segmentation may proceed as described in the paper submitted to 2021 IEEE/RSJ International Conference on Intelligent Robots and Systems (IROS 2021, submission #830). More specifically, the needle localization method begin by running a pre-processed image through a segmentation network. Subsequently, a debiasing operation may be performed to correct detectable false negatives. In the present context, segmentation's most common failure mode may be to falsely identify a linear section of an obstacle boundary as a needle. However, such false positives are consistent in location throughout a single trial of the needle control and are typically shorter than a full needle. Thus, when the needle is fully visible, the localization method may successfully identify it even when a false needle is also present because the longest needle-like object is identified. However, when the needle is partially occluded, the false needle may actually appear longer than the unoccluded portion of the real needle; thus, in such a situation, the false needle may be incorrectly identified as the needle. To address this, a bias, computed as the pixel-wise exponential moving average of the false positive rate, is learned. More specifically, pixels where the bias term is greater than 0.1 are subtracted from the segmentation mask.

Thereafter, the points in the debiased segmentation mask may be clustered using a clustering algorithm, e.g., a Density-based Spatial Clustering of Applications with Noise (DBSCAN), as described in M. Ester, H. P. Kriegel, J. Sander, and X. Xu, *A density-based algorithm for discovering clusters in large spatial databases with noise,* in Proceedings of the Second International Conference on Knowledge Discovery and Data Mining, AAAI Press, 1996, pages 226-231 (incorporated by reference). Clusters with too few points may be discarded as outliers, along with points identified as outliers by DBSCAN. The threshold $N_{min}$ may be computed for discarding a cluster as the square of the needle width. Such a segmentation mask may reliably produce clusters whose width is approximately equal to the needle width, and this threshold may ensure that line detection operations do not utilize clusters whose longer direction is along the needle width. Of note, if no clusters remain following discarding, then the localization would terminate and result in an indication that no needle has been detected.

Subsequently, the set of points belonging to non-discarded clusters may be passed to a random sample consensus (RANSAC) method and used for line detection. See, for example, the RANSAC method as described by M. A. Fischler and R. C. Bolles in *Random sample consensus: A paradigm for model fitting with applications to image analysis and automated cartography*, Communications of the ACM, 1981, volume 24, number 6, pages 381-395 (incorporated by reference).

Of note, the localization procedure may identify the needle angle and visible endpoints, but two ambiguities may remain. First, the RANSAC method operations cannot detect a difference between the needle angle $0 \leq \theta < \pi$ and the corresponding angle $\theta' = \theta + \pi$, $\pi \leq \theta' < 2\pi$. This ambiguity exists because the localization procedures described here are using images (two dimensional data) to represent the three dimensional pose of a needle. In a two dimensional frame, a coordinate axis system with a geometric base orientation of the needle as sitting parallel to the plane of the image may be arranged, pointing north in the frame of the image. With such a base orientation, variables as such: "angle_up" may be defined as the angle of the needle with needle tip pointing up (towards the camera) "angle_down" may be defined as the angle of the needle with needle tip pointing down (away from the camera) "angle_left" and "angle_right" may be defined as the orientation of the tip of the needle within the imaging place captured by the camera, relative to the previously established geometric base orientation. Thus, within the plane imaged by the camera, some ambiguity exists in the context of "angle_up" versus "angle_down", as in both cases the camera sees a two dimensional image in which the length of the projected needle length is the same in both "angle_up" and "angle_down" cases. Nevertheless, accurate needle control requires knowing the correct orientation of the needle. Second, identified endpoints may be the true endpoints of the needle or they may be the points at which the needle disappears under an obstacle or obstruction. Proper occlusion management requires resolving this ambiguity. As a result, both ambiguities may be resolved using the outputs from the segmentation network.

For example, angle_up and angle_left may be used to resolve the angle ambiguity. When the detected angle is closer to 0 or $\pi$ than to $\pm\pi/2$, angle_left may be used to resolve ambiguity, otherwise angle_up may be used. While either of these values, on their own, may be mathematically sufficient, the network's accuracy on angle_up may suffer when the needle is near horizontal, likewise, for angle_left, when the needle is vertical. As a result, selection of which to consider based on the needle angle avoids using the network output in cases where it is less accurate.

Likewise tip_visible and tail_visible may be used to account for occlusion. When these values indicate both endpoints are visible, the center may be computed based on an average of the endpoints. However, when only one endpoint is visible, the center may be computed based on the location of the visible endpoint, the predicted angle, and the known needle dimensions. This may enable the needle localization to accurately identify the needle location even with significant occlusion. In a further case, both endpoints may occluded; thus, a best guess at the needle position may be computed based on the average of the endpoints.

In some examples, the state of the tool may be described using a Hough Line formulation, as described in M. Fan, X. Liu, K. Jain, et al., *Towards autonomous control of magnetic suture needles*, IEEE/RSJ International Conference on Intelligent Robots and Systems (IROS), 2020 (incorporated by reference), which teaches that a Hough Line Transform with appropriate pre-processing and post-processing states in order to estimate a needle pose. More specifically, the image may be prepared by downscaling the raw image, masking the circular work space of the dish, thresholding the image to improve contrast, and applying a Gaussian filter, e.g., using a 0.5 scaling factor, a threshold value of 80, and a 9×9 Gaussian filter, as described. Thereafter, edges may be extracted using a Canny edge detector and a set of line estimates may be generated using the Probabilistic Hough Line Transform. Subsequently, outliers may be removed from collected estimates and an average function may be used to predict a heading of the needle. To predict position, outliers may be removed and a line of best fit is fit to the remaining lines to identify a predicted line. That predicted line may then be compared to a known length of the needle, and the length may be corrected if the estimated needle length is too short by extending the estimate to the known length in the direction of the needle tip using a detected heading. Thereafter, a center of this corrected needle estimate may be used as our positional estimate.

Referring again to FIG. 1, in operation 120 of an example, a computer, optionally, under control of a user or operating in an automated or semi-automated manner, selects the planned position, rotation, and velocity of the tool(s). In some examples, this selection is made using a time-varying trajectory. Examples of mathematical statements of simple trajectories are given in the IROS 2020 publication, for example circular and figure-8 trajectories, as below:

For a circular trajectory, it is possible to demonstrate the needle tracing a circular trajectory characterized by the radius R=0.02 m. The trajectory is represented as follows:

$$r_{dn} = \begin{bmatrix} R\cos\left(\frac{2\pi}{N}n\right) \\ R\sin\left(\frac{2\pi}{N}n\right) \end{bmatrix},$$

where N is the total number of pathway points, n denotes index of the pathway points.

For a number "8" trajectory, the pattern can be parameterized as $$r_{dn} = \begin{bmatrix} R_x\sin\left(\frac{4\pi n}{N}\right) \\ R_y\cos\left(\frac{4\pi n}{N}\right) \end{bmatrix},$$

where Rx and Ry are chosen scaling factors based on the desired pattern dimensions.

Examples of more complex geometries, for example a purse-string geometry, are described in the IROS 2020 publication, listed again below:

The purse-string suture pattern is defined parametrically by the following equation $$r_{dn} = \left(\frac{R_{max} - R_{min}}{2}\cos\left(\frac{2\pi m_d}{N}n\right) + \frac{R_{max} + R_{min}}{2}\right) \begin{bmatrix} \cos\left(\frac{2\pi}{N}n\right) \\ \sin\left(\frac{2\pi}{N}n\right) \end{bmatrix},$$

where $R_{max}$ and $R_{min}$ are set by the user as the outer and inner radii, respectively, of the pattern generated by the purse string manipulation, and, in one example, $m_d=5$, which represents the number of stitches of the purse string suture pattern.

A more general mathematical description of the trajectory is described in the IROS 2021 publication, and restated below:

The reference desired path $r_{des}(t)$ is designed to test the controller and localization algorithms at different regions within the petri-dish and under various visual conditions as described in the next section. The path is designed to achieve a back-and-forth motion of the needle tip, e.g., as required for a running suture. The path is parameterized in time as follows $$r_{des}(t) = \left\{ \frac{(t - t_{i-1})}{(t_i - t_{i-1})}(q_i - q_{i-1}) + q_{i-1}, t \in [t_{i-1}, t_i] \right\}$$

where $q_0, \ldots, q_m$ are the sequence of points that define the shape of the path $t_i=t_{i-1}+\|q_i-q_{i-1}\|/v_{des}$ with $t_0=0$, and $v_{des}$ is the desired speed of the reference point through the path. The derivative of the path is given by $$\dot{r}_{des}(t) = \left\{ v_{des} \frac{(q_i - q_{i-1})}{\|q_i - q_{i-1}\|}, t \in [t_{i-1}, t_i] \right\}$$

Referring again to FIG. 1, in operation 130, magnetic actuators (for example, electromagnets, or electropermanent magnets, or coils) may be used to create magnetic fields in the ROI to implement the trajectory determined at 120. In at least some examples, a non-holonomic method may be used to determine the magnetic fields, as described in IROS 2021 and restated below:

As described in M. Fan, X. Liu, K. Jain, et al., IROS 2020 in detail, and included here for completeness, in this work a dipole model of interaction between the needle and the external magnetic fields generated by the coils is assumed. Under the dipole model, the magnetic fields generated by the $k^{th}$ coil at the location of the needle's center of mass, $r=[x, y]^T$ is given by $$B_k = -\frac{m_k}{\delta_k^3}\left(\hat{r}_k - 3\hat{d}_k\hat{d}_k^T\hat{r}_k\right)I_k$$

where $m_k$ is a constant related to the magnetic properties of the coil, $r_k$ is the center location of the coil, $\hat{r}_k=r_k/\|r_k\|$ is a unit vector. The vector that points from the coil's center to the needle's center of mass is $d_k=r-r_k$, the distance between the coil and the needle is $\delta_k=d_k/\|d_k\|$, $\hat{d}_k=d_k/\delta_k$ is a unit vector, and $I_k$ is the input current at the coil.

The torque and force experienced by the needle due to the magnetic fields generated by the coils is given by the cross product between the needle's magnetic moment vector $M(\theta)$ $=Mh$, where M is a constant related to the needle's magnetic properties and $h=[\cos\theta, \sin\theta]^T$ is a unit vector (pointing in the direction of the tip) and the coil's magnetic field, and the gradient of the magnetic potential, respectively, $$\tau = \sum_{k=1}^{4} M(\theta) \times B_k, \quad F = -\sum_{k=1}^{4} \nabla\left(M(\theta)^T B_k\right).$$

The needle's motion may be assumed to be first-order due to the laminar fluid flow from low Reyolds number and negligible inertia terms, resulting in $$\dot{r} = \frac{r}{c_t}F, \quad \dot{\theta} = \frac{1}{c_r}\tau$$

Where the coefficients $c_t$ and $c_r$ map forces and torques to translation and rotational motion (obtained empirically).

Requiring that the needle's translational motion be kinematically constrained along the length of the needle, ensures the force is applied along the tip of the needle. The nonholomic model becomes $$\begin{bmatrix}\dot{r}\\ \dot{\theta}\end{bmatrix} = \begin{bmatrix} hh^T\frac{F}{c_t} \\ \frac{\tau}{c_r}\end{bmatrix} = \begin{bmatrix}\cos\theta & 0 \\ \sin\theta & 0 \\ 0 & 1\end{bmatrix}g(r,\theta)I = \begin{bmatrix}\cos\theta & 0 \\ \sin\theta & 0 \\ 0 & 1\end{bmatrix}\begin{bmatrix}v\\ \omega\end{bmatrix}$$

Where the needle's linear and angular velocity are given by $$\begin{bmatrix}v\\ \omega\end{bmatrix} = g(r,\theta)I = \sum_{k=1}^{4}g_k(r,\theta)I_k$$

And where is S is a skew-symmetric rotation matrix, $$g_k(r,\theta) = \begin{bmatrix} \frac{3Mm_k}{c_t}\frac{\left(2\hat{d}_k^T hh^T\hat{r}_k + \hat{r}_k^T d_k - 5\left(\hat{d}_k^T h\right)^2\hat{d}_k^T\hat{r}_k\right)}{\delta_k^4} \\ \frac{Mm_k}{c_r}\frac{h^T S\hat{r}_k - 3h^T S\hat{d}_k\hat{d}_k^T\hat{r}_k}{\delta_k^4}\end{bmatrix}$$

Given a desired linear and angular velocity command (v, w), the input currents can be found by employing a pseudo-inverse of the motion vector field relating these, i.e., $$I = g(r,\theta)^T\left(g(r,\theta)g(r,\theta)^T\right)\begin{bmatrix}v\\ \omega\end{bmatrix}.$$

Referring again to FIG. 1, in operation 140, the planned and actual trajectories (optionally including position, rotation, velocity) are compared, and if acceptable match, then proceed to next operation 150, else go back to oparation 110 or operation 120. In some examples, the tool tip (e.g., needle) is tracked as described in IROS 2021, restated below:

In this work, it is of interest to accurately controlling the tip of the needle through the dish. This will be important to ensure the tip penetrates tissue at the desired location as well as avoiding inadvertently damaging surrounding tissue. To this end, a tip-tracking controller is derived to allow the tip of the needle to track a desired reference trajectory. Let $r_{tip}$32 $[x_{tip}, y_{tip}]^T$ by the position of the tip relative to the center position of the needle, r, which is provided by the localization algorithm. As the needle is rigid, the location of the tip is related to the center via $$r_{tip} = r + \frac{\ell}{2}\begin{bmatrix} \cos\theta \\ \sin\theta \end{bmatrix}$$

where $\ell$ is the length of the needle. Differentiating these expressions, we get that $$\dot{r}_{tip} = \dot{r} + \frac{\ell}{2}\begin{bmatrix} -\sin\theta \\ \cos\theta \end{bmatrix}\omega = \begin{bmatrix} \cos\theta \\ \sin\theta \end{bmatrix}v + \frac{\ell}{2}\begin{bmatrix} -\sin\theta \\ \cos\theta \end{bmatrix}\omega$$

which suggests a unique mapping $$\begin{bmatrix} v \\ \omega \end{bmatrix} = \begin{bmatrix} \cos\theta & \sin\theta \\ -\frac{1}{\ell/2}\sin\theta & \frac{1}{\ell/2}\cos\theta \end{bmatrix}\dot{r}_{tip}.$$

Given a differentiable desired reference path $r_{des}(t)$, a PD control strategy is employed to enable tip tracking $$\dot{r}_{tip} = k(r_{des}(t) - r_{tip}) + \dot{r}_{des}(t).$$

If the user and/or computer decides that goal(s) have been attained at 150, then the method proceeds to end the robotic procedure at 170, otherwise it proceeds to determine if the robotic procedure should be aborted at 160, at which, if the user and/or computer decides that robotic procedure should be aborted 160, then the robotic procedure is ended at 170. Otherwise, the method operations return to operation 110.

Figure 3:
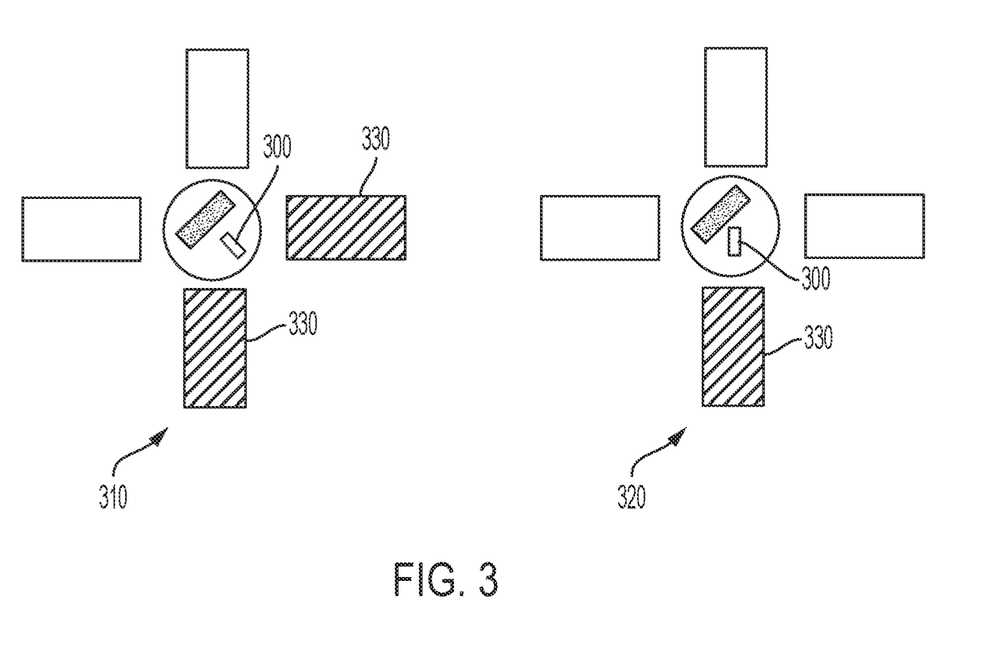
FIG. 3 illustrates a method of actuating the magnetic actuators to create magnetic gradients that manipulate a magnetizable tool according to the disclosed examples.
Figure 4A:
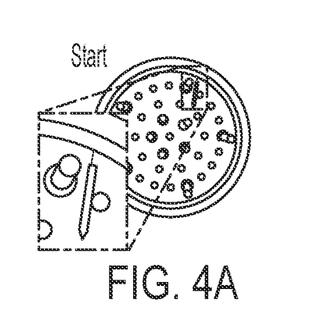
FIG. 4A, FIG. 4B, FIG. 4C, FIG. 4D, FIG. 4E, and FIG. 4F are illustrations of a purse-string type of suture implemented using a system according to the disclosed examples.
Figure 4B:
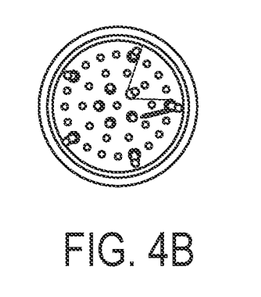
Figure 4C:
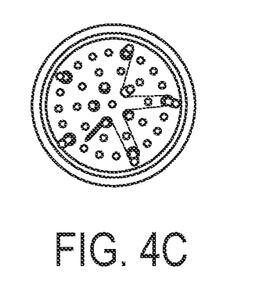
Figure 4D:
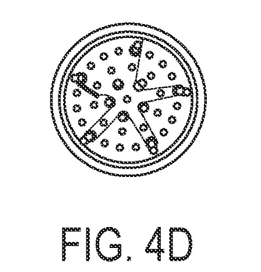
Figure 4E:
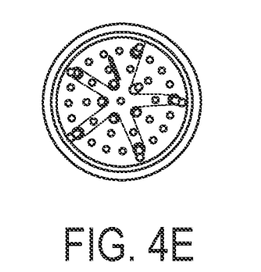
Figure 4F:
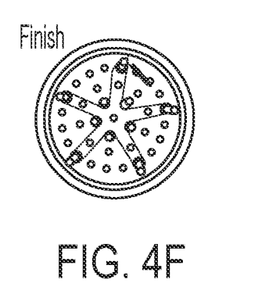

FIG. 3 illustrates an example of a method of actuating the magnetic actuators to create magnetic gradients that manipulate the magnetizable tool 300. A configuration 310 is shown in which two of the magnetic actuators 330 are activated to create a magnetic gradient that aligns tool 300 diagonally in the direction of the gradient. A configuration 320 is shown in which one of the magnetic actuators 330 is activated to create a magnetic gradient that aligns tool 300 in the direction of the magnetic actuator. Many other configurations are possible but are not shown in FIG. 3.

It is possible to push tools using magnetic fields using dynamic inversion, as taught by Irving Weinberg in U.S. Pat. No. 9,694,196, incorporated by reference. In accordance with at least some examples, the state of the tool may be changed (for example, wiggled or vibrated) by magnetic fields in order to enhance visibility with MRI, ultrasound, or other means.

FIG. 4A, FIG. 4B, FIG. 4C, FIG. 4D, FIG. 4E, and FIG. 4F illustrate of a purse-string type of suture implemented using a system as shown in FIG. 3. FIG. 4A, FIG. 4B, FIG. 4C, FIG. 4D, FIG. 4E, and FIG. 4F show how successive manipulations of a tool with an attached suture strong is moved around posts.

As can be readily appreciated, the described examples have the capability to generate and/or measure force so as to perform a purse string suture, a simple interrupted suture, a simple continuous suture, a vertical mattress suture, a horizontal mattress suture, a cruciate suture, a ford interlocking suture, a continuous subcuticular suture, a continuous horizontal mattress suture, a Lembert suture, a Cushing suture, an Everting suture, a lock-stitch suture, a Halsted suture, a Connell suture, a Parker-Kerr suture, or learn new suture patterns as necessary or as devised in medical or veterinary practice. The disclosed examples can also provide forces for other procedures such as creating a sling.

As can be readily appreciated, the disclosed system incorporates acquired images into a force application plan. That force application plan may include knowledge of the magnetization of the surgical instrument or set of instruments, knowledge of the mechanical environment surrounding the surgical instrument or set of instruments, and an understanding of the desired surgical manipulation going forward.

As can readily be appreciated, the disclosed system can be used to manipulate a needle or other surgical instrument for the processes of tissue penetration, tissue ligation, tissue cauterization, or tissue cutting.

A variety of tools may be used with the disclosed examples. In an example, a tool may be a suture needle comprising of a sharpened hard magnetic material onto which is attached a suture thread. In an example, a tool may comprise of a suture needle composed of a hollow hypodermic needle into which permanent hard magnetic materials are inserted and sealed in place. Such a needle may be partially or completely filled with permanent magnetic materials, such as NdFeB, and may be partially or fully sealed at one or both openings of the needle. In an example, a tool may comprise of a needle composed of soft magnetic materials, such as AlNiCo, which has an electrically conducting wire wound around the soft magnetic material. For the purposes of this disclosure, the term "soft" means a material with low enough magnetic coercivity to be magnetized using relatively low electrical currents (for example, less than 1000 amps). The electrically conducting wire has an electrically insulating outer layer and is electrically connected to a controller capable of supplying electrical currents for changing the magnetization of the center needle material with frequencies ranging from DC to 100 kilohertz.

In some examples, the tool may comprise of a needle containing two orthogonally oriented magnetizations, for example as described in U.S. Pat. No. 10,290,404, "METHOD AND APPARATUS FOR NON-CONTACT AXIAL PARTICLE ROTATION AND DECOUPLED PARTICLE PROPULSION" incorporated by reference. In such a needle, the combination of a magnetic gradient combined with a uniform rotating magnetic, the combination of which is called a precessing field, may allow for the needle simultaneously pulled and rotated within the region of interest defined by the surgical system.

It is understood that the sharpness, tip shape, needle dimensions, and needle curvature will affect the amount of force necessary to accomplish tissue penetration using the needle. Information about needle magnetization is augmented by information about tip sharpness, tip shape, needle dimensions, and needle curvature, and this collection of information is used by the controller to adjust the applied currents in coils for force generation. A needle tip of less than 30 microns in minimal diameter would be better for penetration of tissue than a duller tip.

Moreover, those skilled in the art will recognize, upon consideration of the above teachings, that the above exemplary examples may be based upon use of one or more programmed processors programmed with a suitable computer program. However, the disclosed examples could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent examples.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term "non-transitory" is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the examples described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain examples. Such alternative storage devices should be considered equivalents.

The invention claimed is:

1. An apparatus comprising:
a controller;
an imaging device; and
one or more magnetic actuators, wherein one or more magnetizable tools are manipulated by at least one of the one or more magnetic actuators robotically using information about a state of the one or more magnetizable tools collected by the imaging device, wherein the state of the one or more magnetizable tools comprise, a velocity, a magnetization, or combinations thereof,
wherein the controller is configured to operate using a closed-loop control using the information about the state of the one or more magnetizable tools and a density map information of a region of interest and surrounding areas of the region of interest obtained from the imaging device that provides the controller with expected force requirements for moving within the region of interest and the surrounding areas, wherein the closed-loop control comprises proportional-derivative (PD) control, proportional-integral-derivative (PID) control, proportional (P) control, integral (I) control, proportional-integral (PI) control, or proportional-derivative control.

2. The apparatus of claim 1, where the imaging device is configured to perform magnetic resonance imaging to collect the information about the state of the one or more magnetizable tools.

3. The apparatus of claim 1, where the imaging device is configured to perform ultrasound imaging to collect the information about the state of the one or more magnetizable tools.

4. The apparatus of claim 1, where the imaging device is configured to perform optical imaging to collect the information about the state of the one or more magnetizable tools.

5. The apparatus of claim 1, where the imaging device comprises a camera that is configured to perform a combination of one or more of optical, magnetic resonance imaging, or ultrasound imaging to collect the information about the state of the one or more magnetizable tools.

6. The apparatus of claim 1, wherein each of the one or more magnetizable tools comprises one or more current-carrying conductors to alter a magnetic state of a magnetizable material.

7. The apparatus of claim 1, wherein the one or more magnetic actuators are electropermanent magnets.

8. The apparatus of claim 1, wherein the controller is configured to provide control signals to the one or more magnetic actuators to guide the one or more magnetizable tools along a preplanned time-varying trajectory.

9. The apparatus of claim 1, wherein each of the one or more magnetizable tools is a needle comprising magnetizable material.

10. The apparatus of claim 9, wherein each of the one or more magnetizable tools has a sharp tip that has a minimal diameter of 30 microns.

11. The apparatus of claim 9, wherein each of the one or more magnetizable tools is a hollow needle with a magnetizable core.

12. A method of guiding therapeutic procedure or diagnostic procedure in a human or non-human animal comprising:
manipulating a magnetizable tool by one or more magnetic actuators under closed-loop control using images that provide information about a state of the magnetizable tool and a density map information of a region of interest and surrounding areas of the region of interest obtained from the images that provides a controller with expected force requirements for moving within the region of interest and the surrounding areas, wherein the state of the one or more magnetizable tools comprise, a velocity, a magnetization, or combinations thereof,
wherein the closed-loop control comprises proportional-derivative (PD) control, proportional-integral-derivative (PID) control, proportional (P) control, integral (I) control, proportional-integral (PI) control, or proportional-derivative control.

13. The method of claim 12, wherein the therapeutic procedure is to perform ligations.

14. The method of claim 12, wherein the therapeutic procedure is to perform sutures.

15. The method of claim 12, further comprising using a nonholonomic method to determine magnetic fields of the one or more magnetic actuators.

16. The method of claim 12, wherein the closed-loop control comprises machine learning for localization, control, or both localization and control of the magnetizable tool.

17. The method of claim 12, wherein the closed-loop control comprises altering the state of the tool by a magnetic field to enhance segmentation accuracy.

18. The method of claim 12, wherein the manipulating the magnetizable tool by the one or more magnetic actuators further comprising providing a control signals to the one or more magnetic actuators to guide the magnetizable tools along a preplanned time-varying trajectory.

* * * * *